United States Patent [19]

Larkin et al.

[11] Patent Number: 4,970,288

[45] Date of Patent: Nov. 13, 1990

[54] NON-TOXIC POLYESTER COMPOSITIONS MADE WITH ORGANOTIN ESTERIFICATION CATALYSTS

[75] Inventors: William A. Larkin, Avon by the Sea; Emily C. Bossert, Westfield; Edmund M. Gibbons, Somerset, all of N.J.

[73] Assignee: Atochem North America, Inc., Philadelphia, Pa.

[21] Appl. No.: 411,124

[22] Filed: Sep. 22, 1989

[51] Int. Cl.$^5$ .............................................. C08G 63/02
[52] U.S. Cl. .................................. 528/272; 528/283; 524/178; 524/430; 524/784; 428/480; 428/457
[58] Field of Search ............... 528/272, 283; 524/178, 524/430, 784; 428/480, 457

[56] References Cited

U.S. PATENT DOCUMENTS

| | | | |
|---|---|---|---|
| 3,716,523 | 2/1973 | Cook | 528/283 |
| 3,734,890 | 5/1973 | Powanda | 528/238 |
| 3,950,283 | 4/1976 | Wolgemuth | 524/44 |
| 4,014,858 | 3/1977 | Chipman et al. | 528/283 |
| 4,520,188 | 5/1985 | Holzrichter et al. | 528/274 |
| 4,555,542 | 11/1985 | Komatsu et al. | 524/178 |

*Primary Examiner*—John Kight, III
*Assistant Examiner*—Sam A. Acquah
*Attorney, Agent, or Firm*—Stanley A. Marcus

[57] ABSTRACT

Non-toxic organotin catalysts containing at least one direct oxygen-to-tin bond and one direct carbon-to-tin bond are provided for use as esterification catalysts in the production of non-toxic polyester and polyester-containing compositions. Articles made from such polyester and polyester-containing compositions are suitable for use in regulated food, beverage, pharmaceutical, and medical-device applications.

17 Claims, No Drawings

NON-TOXIC POLYESTER COMPOSITIONS MADE WITH ORGANOTIN ESTERIFICATION CATALYSTS

BACKGROUND OF THE INVENTION

The present invention relates to the use of organo-tin esterification catalysts in the production of polyester and polyester-containing compositions, and more particularly to the use of non-toxic catalysts to produce non-toxic compositions suitable for use in food, beverage, pharmaceutical, and medical-device applications.

It is well known that organotin compositions, including organotin oxides, hydroxides, alkoxides and carboxylates, are effective as catalysts in the manufacture of polyester resins and polyester-containing compositions. The use of tin catalysts in the esterification of polyesters is discussed in U.S. Pat. Nos. 2,720,507 issued to Caldwell et al, 3,345,339 issued to Parker et al, and 4,554,344 issued to Jackson et al. The organotin catalysts decrease the time required to complete esterification or transesterification and to effect complete reaction.

Polyester resins and compositions are useful in the manufacture of textiles, coatings, packaging and molded articles. A major application area is in the production of coatings and packages for storing and handling of foods, beverages, and pharmaceuticals and as components of medical devices. When used in such applications, the polyester compositions, and the articles made therefrom, need to be "non-toxic", that is, safe for use by consumers when used for their intended purpose. The compositions and their components generally require the approval of appropriate health-regulatory agencies, such as the U.S. Food and Drug Administration (USFDA). To obtain such approval, prospective users often have to conduct extensive tests, which are both time-consuming and expensive.

Organotin catalysts of the type employed herein have not yet been publicly sanctioned by the USFDA for use in the manufacture of polyesters intended for regulated "food-grade" (as defined by the USFDA) uses, such as food, beverage and pharmaceutical handling and packaging, or medical devices which come into contact with body fluids. Therefore, manufacturers of regulated food-grade polyester resins and polyester-containing compositions, as well as those who fabricate regulated articles therefrom, may resort to less-efficient catalysts or use no catalyst at all. However, the use of less-efficient catalysts, or no catalysts at all, can result in long reaction times with increased costs and energy consumption.

Some users have relied on the assumption that there is zero extraction of the catalyst from contact surfaces into foods, beverages, pharmaceuticals, and body fluids, and that therefore the catalyst is not a "food additive" (as defined by the USFDA), and requires no regulatory sanction. This is, however, an untenable position. Reliance on the assumption of zero extraction of the catalyst from such polyester articles without further testing is faulty, because the extractability of such catalysts from polyester articles into the wide variety of foods, beverages, pharmaceuticals, and body fluids with which they may come into contact is not known, particularly for articles intended for repeated use.

A more desirable situation is one in which the toxicity and extractability of the catalyst has been fully explored and reviewed by scientists experienced in chemistry, polymerization and toxicology so that a scientific judgment can be made and regulations can be published by the appropriate regulatory agency for general use by the public. Such regulations can state the composition of the catalyst material, the purity of the catalyst, the polyester resins and compositions in which the catalyst may be used, acceptable use levels of the catalyst, extraction testing procedures, and extraction limitations. Where the evidence submitted to the regulatory agency clearly demonstrates that the catalyst is of exceptionally low toxicity and only extractable in minute amounts under representative conditions of use in finished articles, the regulatory agency, for example, the USFDA, may conclude that the catalyst material may be used for its intended technical effect without requiring additional extraction testing by particular users, such as polyester manufacturers and article fabricators.

SUMMARY OF THE INVENTION

The present invention provides non-toxic organotin catalysts suitable for use in the production of non-toxic polyester and polyester-containing compositions. The organotin catalysts for use in the present invention all include at least one direct carbon-to-tin bond and one direct oxygen-to-tin bond. They can be described by the general formula:

$$R_m Sn(OX)$$

in which

R may be the same or different when more than one R is present,

R is an alkyl of 1 to about 20 carbon atoms, or an aryl, alkaryl or cycloalkyl of 6 to about 4 carbon atoms, and R may be saturated or unsaturated, substituted or unsubstituted; and m may equal 1 or 2, provided that when $m=1$, (OX) represents $O_{1.5}$, (O)OH or $(OR')_3$; and when $m=2$, (OX) represents O or $(OR')_2$;

wherein R' may be the same or different when more than one R' is present, and

R' is hydrogen, an alkyl of 1 to about 20 carbon atoms, or the residue of a monofunctional or multifunctional alcohol, carboxylic acid, or ester;

provided that when R' is the residue of a multifunctional alcohol, carboxylic acid, or ester, including one having two or more hydroxyl groups, two or more carboxylic acid groups, or one of each, then the organotin compound may contain two or more organotin moieties in the same molecule bonded to each other through the residue of the multifunctional anion, such that in each instance in which a multifunctional anion is attached to two or more tin atoms, the organotin catalyst may be a dimer, a trimer or a higher molecular-weight polymer; and furthermore, when (OX) represents $(OR')_2$ or $(OR')_3$, one or two of the (OR') groups, respectively, may be replaced by an anion bonded to the tin through a non-oxygen atom, such as sulfur, phosphorus, or nitrogen, or a monovalent ion, such as a halide, bonded directly to the tin.

Preferably, the non-toxic organotin catalysts of the present invention are characterized by having an $LD_{50}$ of at least 0.75 grams/kilogram (g/kg) when fed to rats, and an extractability from polyester and polyester-containing compositions and articles of not more than 200 parts per billion (ppb) when extracted with water, corn oil, or heptane, using the procedures taught in Title 21 of the U.S. Code of Federal Regulations. In addition, the catalysts preferably have a triorganotin content of less than about 5 percent, and a heavy-metal content of less than about 200 parts per million (ppm). Furthermore, each component organotin compound preferably has a purity of at least about 90 percent.

The non-toxic organotin catalysts of the present invention are suitable for use in the production of non-toxic polyester resins and compositions intended for contact with foods, beverages, and pharmaceuticals and in medical devices. The organotin catalysts are of sufficiently low toxicity, low extractability, and high purity to allow their use in such polyesters without further extraction testing by the users.

The invention also includes non-toxic polyester-containing articles in the form of coatings, bottles, packages, tubes, molded products, textiles, and film and sheet intended for packaging and handling foods, beverages, and pharmaceuticals, and for use in medical devices. The polyester article of this process is characterized by extractability of the residual catalyst at levels acceptable to government regulatory agencies without resort to further extraction testing, typically 200 ppb or less.

Furthermore, this invention provides a process for the manufacture of non-toxic polyester resins and polyester-containing compositions. The process of the present invention comprises the step of catalyzing a polyester esterification or transesterification reaction with the organotin catalysts described herein, leaving residual catalyst in the polyester article.

DETAILED DESCRIPTION OF THE INVENTION

The organotin catalyst for preparing non-toxic polyester resin in accordance with the present invention is employed at a concentration of about 0.01–1.0 percent by weight (wt. %) based on the weight of polyester resin. (All percents herein are expressed as percents by weight, unless otherwise indicated.) A preferred concentration is about 0.05–0.2 wt. %. It may be advantageous to use a mixture of such catalysts. Therefore for purposes of this application, reference to "a catalyst" in accordance with this invention is intended to denote reference to one or more catalysts in accordance with the below general formula.

The organotin catalysts for use in the present invention all include at least one direct carbon-to-tin bond and one direct oxygen-to-tin bond. They can be described by the general formula:

$$R_m Sn(OX)$$

in which

R may be the same or different when more than one R is present,

R is an alkyl of 1 to about 20 carbon atoms, or an aryl, alkaryl or cycloalkyl of 6 to about 14 carbon atoms, and R may be saturated or unsaturated, substituted or unsubstituted; and m may equal 1 or 2, provided that when m=1, (OX) represents $O_{1.5}$, (O)OH or $(OR')_3$; and when m=2, (OX) represents O or $(OR')_2$;

wherein R' may be the same or different when more than one R' is present, and

R' is hydrogen, an alkyl of 1 to about 20 carbon atoms, or the residue of a monofunctional or multifunctional alcohol, carboxylic acid, or ester;

provided that when R' is the residue of a multifunctional alcohol, carboxylic acid, or ester, including one having two or more hydroxyl groups, two or more carboxylic acid groups, or one of each, then the organotin compound may contain two or more organotin moieties in the same molecule bonded to each other through the residue of the multifunctional anion, such that in each instance in which a multifunctional anion is attached to two or more tin atoms, the organotin catalyst may be a dimer, a trimer or a higher molecular-weight polymer; and furthermore, when (OX) represents $(OR')_2$ or $(OR')_3$, one or two of the (OR') groups, respectively, may be replaced by an anion bonded to the tin through a non-oxygen atom, such as sulfur, phosphorus, or nitrogen, or a monovalent ion, such as a halide, bonded directly to the tin.

Preferably, the organotin catalysts of the non-toxic polyester compositions of the present invention are characterized by having an $LD_{50}$ of at least 0.75 g/kg when fed to rats and an extractability from polyester and polyester-containing compositions and articles of not more than 200 ppb, when extracted with water, corn oil, or heptane, using the procedures taught in Title 21 of the U.S. Code of Federal Regulations. Suitable procedures for conducting such tests are set forth below.

The triorganotin content of the catalysts of the present invention should preferably be less than about 5 percent. Triorganotin compounds (i.e. m=3 in the above formula) do not fall within the scope of the above formula, but are often undesirable biproducts in the manufacture of other organotin compounds. Because triorganotin compounds are generally considered toxic, their content in the catalysts should be minimized. Heavy metals are also undesirable impurities, and, therefore, the heavy-metal content of the catalyst is preferably less than about 200 parts per million (ppm).

The organotin catalysts of the present invention may comprise one or more organotin compounds in accordance with the above formula. However, each component organotin compound should preferably have a purity of at least about 90 percent.

Examples of the non-toxic organotin catalysts of this invention exemplified by the generic formula $R_{(m)}Sn(OX)$ include:

Organotin Oxides—of the type $R_2SnO$:

Bis (carbomethoxyethyl) tin oxide
Diallyltin oxide
Dibenzyltin oxide
Dibutyltin oxide
Dicyclohexyltin oxide
Didodecyltin oxide
Diisobutyltin oxide
Dimethyltin oxide
Di-1-naphthyltin oxide
Dioctyltin oxide
Diphenyltin oxide
Di-o-tolyltin oxide
Divinyltin oxide.

Organotin Hydroxides—of the type $R_2Sn(OH)_2$ or $R_2Sn(OH)Y$, wherein Y is a halide:

Dibutylchlorotin hydroxide
Dicyclohexyltin dihydroxide
Dibutyltin dihydroxide
Dibenzyltin dihydroxide
Didodecyltin dihydroxide
Dimethyltin dihydroxide
Dioctyltin dihydroxide
Di-o-tolyltin dihydroxide.

Organotin Alkoxides—of the type $R_2Sn(OR')_2$ or $R—Sn(OR')_3$:

Dibutyl bis (benzyloxy) tin
Didodecyl bis (benzyloxy) tin
Dibutyldibutoxytin
Dimethyldibutoxytin
Dibutyldimethoxytin
Dibutyldiphenoxytin
Dibutyltin (0,0) - bis (methylricinoleate)
Monobutyltin trimethoxide
Monobutyltin tributoxide
Monomethyltin trimethoxide
Monomethyltin tributoxide
Dibutylmethoxybutoxytin
Dibutyltin ethylene glycoxide.

Organostannoic Acids—of the type $R—SnOOH$, or their corresponding anhydrides of the type $(RSnO)_2O$:

Phenylstannoic acid
Chlorobenzylstannoic acid
1-dodecenylstannoic acid
Methylstannoic acid
1-naphthylstannoic acid
p-tolylstannoic acid
Butylstannoic acid
Octylstannoic acid.

Carboxylic Acid Derivatives—of the type $R_2Sn(O_2CR')_2, R_2Sn(O_2CR')(OCR')$, $R—Sn(O_2CR')_3$, or $R—Sn(O_2CR')_2Y$, wherein Y is a halide:

Dibenzyltin diacetate
Dibenzyltin distearate
dibutylmethoxytin acetate
Dibutylmethoxytin butylmaleate
Dibutyltin bis (methylmaleate)
Dibutyltin dilaurate
Dimethyltin diacetate
Dibutyltin phthalate
Dibutyltin maleate
Dibutyltin oxalate
Dibutyltin terephthalate
Dioctyltin diacetate
Dioctyltin dilaurate
Diphenyltin diacetate
Divinyltin dilaurate
Methyltin trilaurate
Methyltin triacetate
Methyltin tris (2-ethylhexoate)
Butyltin trilaurate
Butyltin triacetate
Butyltin tris (2-ethylhexoate)
Butyltin tris (lauryl maleate).
Butyltin bis (2-ethylhexoate) chloride Preferred non-toxic organotin catalysts include, but are not limited to, hydroxybutyltin oxide (also known as butylstannoic acid), monobutyltin tris (2-ethylhexoate), and dibutyltin oxide.

Toxicity Studies

The $LD_{50}$ test procedure was as follows:

Albino rats were administered the test materials by oral intubation. Following dosing, the rats were housed with food and water. Observations were made periodically during the first day and daily for fourteen days following. The results were as follows:

| Test Material | $LD_{50}$ |
| --- | --- |
| Hydroxy butyltin oxide | >20 g/kg |
| Butyltin tris (2-ethylhexoate) | >3200 mg/kg |
| Dibutyltin oxide | >794 mg/kg |

Extraction Studies

Polyester resin was prepared from the reaction of isophthalic acid, maleic anhydride, propylene glycol and dipropylene glycol with and without tin catalysts. At the completion of the esterification reaction, the resin was diluted with styrene. Polyester plaques were prepared from these resins by addition of a peroxide to catalyze the reaction of the maleate unsaturation with styrene. Extraction studies were conducted using corn oil, water and heptane as the extractants.

The corn-oil extraction studies were carried out by exposing the plaques to corn oil at temperatures from $-18°$ C. to $190°$ C. for 45 minutes. Organic matter in the oil extract was destroyed by acid digestion, and the amount of tin extracted was determined by atomic-absorption spectroscopy.

The water-extraction studies were carried out by exposure of cured plaques to water in a sealed vial at $190°$ C. for three hours and at $160°$ C. for ten days. The water extract was then analyzed for tin by atomic-absorption spectroscopy.

The heptane-extraction studies were carried out by exposure of the cured plaques to heptane at $130°$ C. for two hours. The heptane extract was then analyzed for tin by atomic-absorption spectroscopy.

The results of the extraction studies are shown in Tables 1, 2, and 3 below.

TABLE 1

ANALYSES OF TIN EXTRACTED INTO OIL FROM CURED POLYESTER PLAQUES

| Catalyst | Tin in Resin (ppm) | Extracted Tin (ppb) |
| --- | --- | --- |
| A | 216 | 6 |
| B | 513 | 16 |
| C | 213 | 1 |
| C | 299 | 4 |
| C | 266 | 1 |
| C | 269 | 1 |
| none | 0 | 1 |

A = monobutyltin tris (2-ethylhexoate)
B = dibutyltin oxide
C = hydroxybutyltin oxide

TABLE 2

ANALYSES OF TIN EXTRACTED INTO WATER FROM CURED POLYESTER PLAQUES

| Catalyst | Tin in Resin (ppm) | Extracted Tin (ppb) |
| --- | --- | --- |
| A | 216 | <1 |
| B | 513 | 27 |
| C | 213 | 3 |

TABLE 2-continued
ANALYSES OF TIN EXTRACTED INTO WATER FROM CURED POLYESTER PLAQUES

| Catalyst | Tin in Resin (ppm) | Extracted Tin (ppb) |
|---|---|---|
| C | 299 | 3 |
| C | 266 | 1 |
| C | 269 | <1 |
| none | 0 | <1 |

A = monobutyltin tris (2-ethylhexoate)
B = dibutyltin oxide
C = hydroxybutyltin oxide

TABLE 3
ANALYSES OF TIN EXTRACTED INTO HEPTANE FROM CURED POLYESTER PLAQUES

| Catalyst | Tin in Resin (ppm) | Extracted Tin (ppb) |
|---|---|---|
| A | 216 | 4 |
| B | 513 | 3 |
| C | 260 | 3 |
| none | 0 | 3 |

A = monobutyltin tris (2-ethylhexoate)
B = dibutyltin oxide
C = hydroxybutyltin oxide While the inventors do not wish to be bound by any particular theory related to the surprisingly low extractability of these organotin catalysts, it is proposed that the minute quantities extracted, 200 ppb or less, may be due to conversion of these organotin catalysts containing at least one carbon-to-tin bond to inorganic tin compounds at the elevated temperature at which the polyester is produced. Alternatively, these organotin catalysts containing at least one carbon-to-tin bond may be tightly bound in the polyester matrix either chemically or physically. Whatever mechanism is responsible, the minute extractability by oil, water and heptane make these catalysts suitable for use in non-toxic polyester-containing compositions intended for use in regulated food, beverage, pharmaceutical, and medical-device applications.

Polyester Definition

Polyesters for use in the non-toxic compositions of the present invention are the polycondensation product of one or more polyfunctional carboxylic acids, acid anhydrides, or esters with one or more polyhydroxyl alcohols. In addition there may be a monofunctional acid or alcohol end group.

Linear polyesters are prepared from the polycondensation of a dicarboxylic acid with a glycol. When a portion of the alcohol or acid components has a functionality greater than two, the structure may be cross-linked.

The acid and alcohol components may be aromatic, aliphatic, or mixed aromatic and aliphatic. Among the acceptable components are those listed in various USFDA regulations in Title 21 of the U.S. Code of Federal Regulations (CFR), including 21 CFR 177.2420 (a)(1), 21 CFR 175.300 (b)(3)(vii)(a) and (b), 21 CFR 175.320(b)(3), 21 CFR 176.320(a)(5) and (b)(2), 21 CFR 177.1590(a), 21 CFR 177.660(a), and 21 CFR 177.1680(a)(2). In addition, monobasic acids, listed in 21 CFR 175.300 (b)(3)(vii)(b), may be used as chain stoppers.

In addition, the polyesters may be those described in 21 CFR 177.1240 and 21 CFR 177.1315.

The mole ratio of hydroxyl groups to acid groups theoretically is one to one; however, excess hydroxyl or acid groups may be used, depending on the end use of the polyester.

The tin catalysts of this invention are used in the esterification reaction in the manufacture of polyester resins. These resins may be used directly by thermoforming or may be cured by reaction with a cross-linking agent using an appropriate catalyst which may or may not contain tin.

Preferred polyesters for forming non-toxic compositions with tin catalysts in accordance with the present invention include:

isophthalate-propylene glycol-maleate copolymer cured by reaction with styrene and peroxide-based catalyst;

polybutylene terephthalate;

polyethylene terephthalate; and the reaction product of 2,2,4-trimethyl-1,3-pentanediol, trimethylol propane, isophthalic acid, and adipic acid cured with a cross-linking agent.

Examples of Catalyst Use in Resin Synthesis

The importance of catalyst use in decreasing reaction time is illustrated by the following example:

Into a 2-liter, 3-neck reaction flask equipped with an $N_2$ inlet tube, air stirrer, pot thermometer, partial steam-heated condenser, and a receiver with full condenser, the following reagents were charged:

| | |
|---|---|
| Propylene glycol | 4.4 moles (334 g) |
| Isophthalic acid | 2.0 moles (332 g) |

The reaction mixture was heated to a maximum temperature of about 220° C., driving off the water of reaction. When the acid number, determined by titration with alcoholic KOH, reached approximately 10 milligrams KOH per gram (mg KOH/g) of sample, the reaction mass was cooled to about 160° C. and 2.0 moles (196 g) of maleic anhydride was added.

The reaction mass was heated again to about 220° C. and reaction continued, with removal of water, until the acid number reached 25 mg KOH/g sample.

A second reaction was carried out in the same manner, except that 0.86 g hydroxy monobutyltin oxide (MBTO) (0.20 mole % of initial charge) was added initially.

The reaction times for the two procedures are shown below:

| Reaction Condition | First Stage Time in Hours | Second Stage Time in Hours |
|---|---|---|
| No catalyst | 6.3 | 5.6 |
| 0.20 mole % MBTO | 2.9 | 4.5 |

Similar reductions in reaction time were obtained in comparative tests using equivalent molar amounts of dibutyltin oxide and monobutyltin tris (2-ethylhexoate) as the catalysts. These results demonstrate that the use of such tin catalysts can greatly reduce reaction time.

Synthesis of Typical Organotin Compounds

Synthesis of organotin compounds is usually carried out by the condensation reaction of $R_mSnCl_{4-m}$ with the acid or sodium salt of the desired OX groups, followed by washing with water and drying. Typical examples follow:

Dibutyltin oxide (DBTO):

Dibutyltin oxide is produced by the reaction of dibutyltin dichloride of at least 95% purity with an aqueous solution of sodium hydroxide. The product is washed with water centrifuged and dried. A yield of 99%, based on the dichloride charge, is expected. The purity is typically at least 95%, with less than 1% tributyltin oxide, less than 1.5% monobutyltin oxide, less than 1% moisture, and less than 200 ppm heavy metals.

Hydroxy monobutyltin oxide (MBTO): MBTO is produced by the addition of an aqueous solution of monobutyltin trichloride of 95% purity to an aqueous solution of sodium hydroxide. The product is washed with water, centrifuged, and dried. A yield of about 95% is expected. The MBTO is generally at least 95% pure, with typical impurities including dibutyltin oxide, tributyltin oxide, moisture, and less than 200 ppm heavy metals.

Butyltin tris(2-ethylhexoate):

Butyltin tris(2-ethylhexoate) is produced by the reaction of aqueous monobutyltin trichloride of 95% purity with the sodium salt of 2-ethylhexanoic acid. The liquid product is separated, vacuum-stripped, cooled, and filtered. A yield of 98% is expected. The purity is typically at least 95%, with impurities including di- and tributyltin 2-ethylhexoates, 2-ethylhexanoic acid, and less than 200 ppm heavy metals.

The terms and expressions which have been employed are used as terms of description and not of limitation, and there is no intention, in the use of such terms and expressions, of excluding any equivalents of the features shown and described or portions thereof, but it is recognized that various modifications are possible within the scope of the invention claimed.

What is claimed is:

1. A non-toxic polyester or polyester-containing composition adapted for the handling and packaging of foods, beverages, or pharmaceuticals, or for use in medial devices comprising a polyester resin which has been esterified with an organotin catalyst at a level of about 0.01 to 1 percent by weight of the polyester, wherein the organotin catalyst is characterized by having an $LD_{50}$ of at least about 0.75 g/Kg when fed to rats; an extractability from polyester and polyester-containing compositions and articles of less than about 200 ppb when extracted ;with water, corn oil or heptane; a triorgaotin content of less than about 5 percent by weight; and a heavy-metal content of less than about 200 ppm, and comprises one or more compounds of the formula:

in which
R may be the same or different when more than one R is present,
R is an alkyl of 1 to about 20 carbon atoms, or an aryl, alkaryl or cycloalkyl of 6 to about 14 carbon atoms, and
R may be saturated or unsaturated, substituted or unsubstituted; and
m may equal 1 or 2, provided that
when m=1, (OX) represents $O_{1.5}$, (O)OH or $(OR')_3$; and
when m=2, (OX) represents O or $(OR')_2$;
wherein R' may be the same or different when more than one R' is present, and
R' is hydrogen, an alkyl of 1 to about 20 carbon atoms or the residue of a monofunctional or multifunctional alcohol, carboxylic acid or ester;

provided that when R' is the residue of a multifunctional alcohol, carboxylic acid, or ester, including one having two or more hydroxyl groups, two or more carboxylic acid groups, or one of each, then the organotin compound may contain two or more organotin moieties in the same molecule bonded to each other through the residue of the multifunctional anion, such that in each instance in which a multifunctional anion is attached to two or more tin atoms, the organotin catalyst may be a dimer, a trimer or a higher-molecular-weight polymer; and provided further that when (OX) represents $(OR')_2$ or $(OR')_3$, one or two of the (OR') groups, respectively, may be replaced by an anion bonded to the tin through a non-oxygen atom or a monovalent ion bonded directly to the tin.

2. The non-toxic composition of claim 1 in which said organotin catalyst is further characterized by a purity for each component organotin compound of at least about 90 percent by weight.

3. The non-toxic composition of claim 1 wherein said organotin catalyst is used at a level of about 0.05 to 0.2 percent by weight.

4. The non-toxic composition of claim 1 wherein said organotin catalyst comprises at least one organotin oxide, hydroxide, alkoxide, or carboxylate.

5. The non-toxic composition of claim 1 wherein said organotin catalyst comprises at least one of hydroxybutyltin oxide, monobutyltin tris (2-ethylhexoate), or dibutyltin oxide.

6. A composition adapted for the handling and packaging of foods, beverages or pharmaceuticals, or for use in medical devices comprising a polyester resin which has been esterified with an organotin catalyst having at least one direct carbon-to-tin bond and one direct oxygen-to-tin bond, said catalyst being characterized by an $LD_{50}$ of at least about 0.75 g/Kg when fed to rats, an extractability from said composition of less than about 200 ppb when extracted with water, corn oil or heptane, a triorganotin content of less than about 5 percent by weight and a heavy-metal content of less than about 200 ppm.

7. The polyester products of claim 6 wherein said products are in the form of coatings, tank linings, film, sheet, fibers, tubes, bottles, packages or molded articles.

8. The polyester products of claim 6 wherein said products are in the form of food can liners, bulk storage tanks, beverage bottles, food wraps, blood bags, transfusion tubing, and pharmaceutical packaging.

9. A process for manufacturing non-toxic polyester resins which are made by esterification comprising the step of employing 0.01 to 1.0 percent by weight of an organotin catalyst as set forth in claim 1 in the esterification of the resin.

10. A non-toxic organotin catalyst for use at a level of about 0.01 to 1 percent by weight in the esterification of polyester resins for use in non-toxic polyester or polyester-containing composition, said organotin catalyst comprising one or more compounds of the formula:

in which
R may be the same or different when more than one R is present,
R is an alkyl of 1 to about 20 carbon atoms, or an aryl, alkaryl or cycloalkyl of 6 to about 14 carbon atoms, and R may be saturated or unsaturated, substituted or unsubstituted; and m may equal 1 or 2, provided that when m=1,(OX) represents $O_{1.5}$,(O)OH or (OR')$_3$; and when m=2,(OX) represents O or (OR')$_2$;

wherein R' may be the same or different when more than one R' is present, and

R' is hydrogen, an alkyl of 1 to about 20 carbon atoms or the residue of a monofunctional or multifunctional alcohol, carboxylic acid, or ester;

provided that when R' is the residue of a multifunctional alcohol, carboxylic acid, or ester, including one having two or more hydroxyl groups, two or more carboxylic acid groups, or one of each, then the organotin compound may contain two or more organotin moieties in the same molecule bonded to each other through the residue of the multifunctional anion, such that in each instance in which a multifunctional anion is attached to two or more tin atoms, the organotin catalyst may be a dimer, a trimer or a higher-molecular-weight polymer; and provided further that when (OX) represents (OR')$_2$ or (OR')$_3$, one or two of the (OR') groups, respectively, may be replaced by an anion bonded to the tin through a non-oxygen atom or a monovalent ion bonded directly to the tin;

and further provided that said non-toxic organotin catalyst is characterized by having an $LD_{50}$ of at least about 0.75 g/kg when fed to rats; an extractability from polyester and polyester-containing compositions and articles of less than about 200 ppb when extracted with water, corn oil or heptane; a triorganotin content of less than about 5 percent by weight; a heavy-metal content of less than about 200 ppm; and a purity for each component organotin compound of at least about 90 percent by weight.

11. The non-toxic organotin catalyst of claim 10 comprising at least one organotin oxide, hydroxide, alkoxide, or carboxylate.

12. The non-toxic organotin catalyst of claim 10 comprising at least one of hydroxybutyltin oxide, monobutyltin tris (2-ethylhexoate), or dibutyltin oxide.

13. A food, beverage or pharmaceutical product in contact with a polyester or polyester-containing composition comprising a polyester resin which has been esterified with an organotin catalyst at a level of about 0.01 to 1 percent by weight of the polyester, wherein the organotin catalyst is characterized by an $LD_{50}$ of at least about 0.75 g/Kg when fed to rats; an extractability from polyester and polyester-containing compositions and articles of less than about 200 ppb when extracted with water, corn oil or heptane; a triorganotin content of less than about 5 percent by weight; a heavy-metal content of less than about 200 ppm; and a purity for each component organotin compound of at least about 90 percent by weight, and wherein the organotin catalyst comprises a compound of formula;

in which

R may be the same or different when more than one R is present, R is an alkyl of 1 to about 20 carbon atoms, or an aryl, alkaryl or cycloalkyl of 6 to about 14 carbon atoms, and R may be saturated or unsaturated, substituted or unsubstituted; and m may equal 1 or 2, provided that when m=1,(OX) represents $O_{1.5}$,(O)OH or (OR')$_3$; and when m=2,(OX) represents O or (OR')$_2$;

wherein R' may be the same or different when more than one R' is present, and

R' is hydrogen, an alkyl of 1 to about 20 carbon atoms or the residue of a monofunctional or multifunctional alcohol, carboxylic acid, or ester;

provided that when R' is the residue of a multifunctional alcohol, carboxylic acid, or ester, including one having two or more hydroxyl groups, two or more carboxylic acid groups, or one of each, then the organotin compound may contain two or more organotin moieties in the same molecule bonded to each other through the residue of the multifunctional anion, such that in each instance in which a multifunctional anion is attached to two or more tin atoms, the organotin catalyst may be a dimer, a trimer or a higher-molecular-weight polymer; and provided further that when (OX) represents (OR')$_2$ or (OR')$_3$, one or two of the (OR') groups, respectively, may be replaced by an anion bonded to the tin through a non-oxygen atom or a monovalent ion bonded directly to the tin.

14. The product of claim 13 in which the organotin catalyst comprises an organotin oxide, hydroxide, alkoxide or carboxylate.

15. The product of claim 13 in which the organotin catalyst comprises hydroxybutyltin oxide, monobutyltin tris (2-ethylhexoate), or dibutyltin oxide.

16. The product of claim 13 in which the polyester or polyester-containing composition is in the form of a coating, tank lining, film, sheet, fiber, tube, bottle, package or molded article.

17. The product of claim 13 in which the polyester or polyester-containing composition is in the form of a food can liner, bulk storage tank, beverage bottle, food wrap, transfusion tubing, blood bag or other pharmaceutical packaging.

* * * * *